United States Patent

De Carvalho et al.

[11] Patent Number: 5,962,106
[45] Date of Patent: Oct. 5, 1999

[54] ABSORBENT PRODUCT

[75] Inventors: Antonio Carlos Ribeiro De Carvalho, Sao Paul; Paulo Roberto Amaral Serra, Sao Joe dos Campos, both of Brazil

[73] Assignee: Johnson & Johnson Ind. E. Com. Ltda, Sao Paulo, Brazil

[21] Appl. No.: 08/923,303

[22] Filed: Sep. 4, 1997

[30] Foreign Application Priority Data

Sep. 2, 1996 [BR] Brazil ........................................ 9603634

[51] Int. Cl.[6] ................................ B32B 3/24; A61F 13/46
[52] U.S. Cl. ........................ 428/131; 428/137; 428/138; 428/913; 604/382; 604/378; 604/383
[58] Field of Search ................................ 428/913, 131, 428/137, 138; 604/382, 378, 383

[56] References Cited

U.S. PATENT DOCUMENTS

| | | | |
|---|---|---|---|
| 3,559,649 | 2/1971 | Grad et al. | 128/290 |
| 3,799,167 | 3/1974 | Miller et al. | 128/287 |
| 4,015,604 | 4/1977 | Csillag | 128/287 |
| 4,413,996 | 11/1983 | Taylor | 128/284 |
| 5,308,344 | 5/1994 | Toth | 604/378 |
| 5,401,266 | 3/1995 | Runeman et al. | 604/378 |
| 5,533,991 | 7/1996 | Kirby et al. | 604/383 |
| 5,746,729 | 5/1998 | Wada et al. | 604/378 |
| 5,853,401 | 12/1998 | Mayer et al. | 604/378 |
| 5,855,719 | 1/1999 | Menard | 156/256 |
| 5,891,118 | 4/1999 | Toyoshima et al. | 604/366 |

FOREIGN PATENT DOCUMENTS

| | | |
|---|---|---|
| 0523683 | 1/1993 | European Pat. Off. . |
| 0523719 | 1/1993 | European Pat. Off. . |
| 2262235 | 6/1993 | United Kingdom . |
| 93/12745 | 7/1993 | WIPO . |
| 95/10254 | 4/1995 | WIPO . |

Primary Examiner—William P. Watkins, III

[57] ABSTRACT

The present invention refers to an absorbent product, especially a sanitary napkin (1), including an absorbent body (2) characterised by having a first portion (5) of perforated plastic film (6) and, on the surface (13) adapted to come into contact with the user's body, a longitudinal layer which includes a second central portion (7) of woven or non-woven material on the body contact surface (13), the first portion (5) being at least near the side edges (11) of the absorbent body (2) at the contact surface and having the thickness of the absorbent body (2)

7 Claims, 1 Drawing Sheet

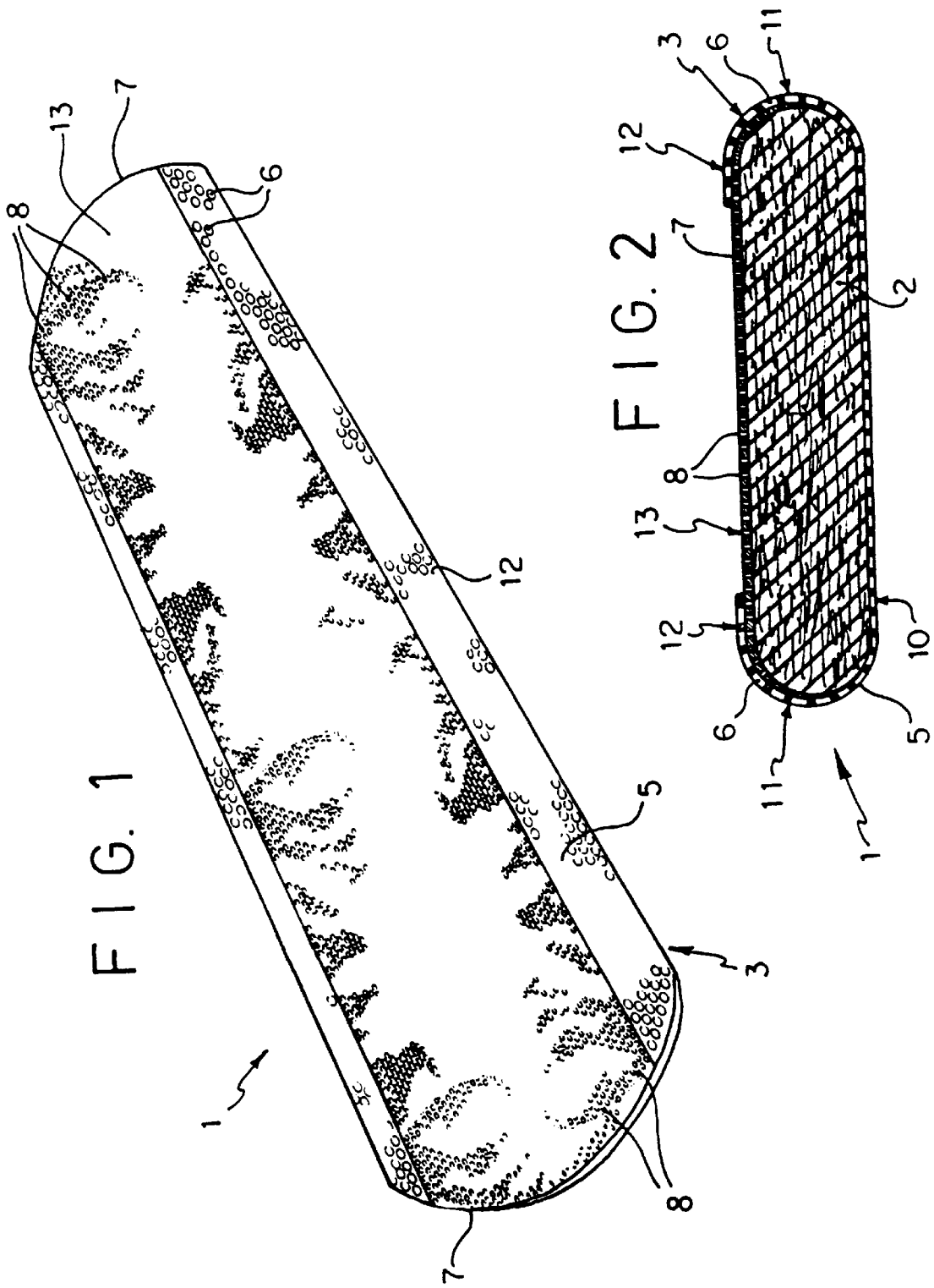

ABSORBENT PRODUCT

FIELD OF THE INVENTION

The present invention refers to an absorbent product, preferably a disposable sanitary napkin for women, with a top layer that comes in contact with the user's body—with a longitudinal central band made of non-fabric material and. a perforated plastic film covering the rest of the top layer, the sides of the above mentioned. napkin and. possibly the bottom layer.

BACKGROUND OF THE INVENTION

As is known in the art, feminine sanitary napkins are generally disposable and. used. to collect and contain vaginal exudates, especially menstrual bleeding, intermenstrual secretions and even urine in cases of incontinence.

Typically, these sanitary napkins are made up of an elongated. body made of absorbent material, covered. by an external at least partially liquid permeable layer, at least on the top side which comes into contact with the users body.

As the above mentioned sanitary napkin becomes saturated. with liquid, the possibility of leaking increases, because of two main reasons:

new discharges of liquid will have less chance of being absorbed, as there is less absorbent material available; and part of the liquid inside the absorbent material may eventually be exuded, especially when the user moves, compressing and. deforming the sanitary napkin.

Some prior art patent documents refer to sanitarty napkins or diapers which have a perforated. plastic film in the central longitudinal area on the part that comes into contact with the user's body, and non-woven on that same side in the areas near the edges and throughout the thickness of the product. WO 9312745 and. WO 9510254 of Moelnlycke and EP 523683 and EP 523719 of Kimberly-Clark can be cited.

These documents have as a common denominator the concern with leaking and comfort. They propose perforated plastic films on the user's body contact surface, as being presumably more efficient for retaining liquids, and non-wovens at the sides of the absorbent product, as being presumably more pleasant to touch the user's skin. Nonetheless, it is known that the plastic film surface is a reason for discomfort, for those users who complain about the feeling of swelter (thus prejudicing comfort) while the non-woven at the sides of the product is a subtrate which may potentially lead liquids through its structure which is provided with interstices (whereby protection against leaking may be improved).

This technology is different from that of the present invention, and there is no hint in those documents that show the invention results from the former.

Still referring to the prior art, GB patent application 2.262.235 of Nov. 27, 1992 discloses that the intermediate body of absorbent material is wrapped with a bottom liquid permeable film, a top perforated plastic film and side bands of imperforate embossed plastic.

SUMMARY OF THE INVENTION

The object of this invention is to prevent sideways leaking of the liquid that has already been absorbed into the absorbent core, but the level of comfort is still subject to improvement, bearing in mind the feeling of swelter mentioned by some users of sanitary napkins with the perforated plastic films in contact with the body. This technology also differs from the one now presented and there are no indications that suggest that it is a result of the former.

BRIEF DESCRIPTION OF THE SEVERAL VIEWS OF THE DRAWING

FIG. 1 is a perspective view of a sanitary napkin representing the preferred shape of this invention;

FIG. 2 is a cross cut of the sanitary napkin of FIG. 1 taken through lines 2—2.

DETAILED DESCRIPTION OF THE INVENTION

It is desirable, therefore, to provide a sanitary napkin which will meet the needs stated above, which are to decrease or prevent that feeling of swelter due to the plastic film coming into contact with the user's body and to improve the barrier against sideways leaking.

According to the present invention, these goals are met by means of an absorbent product which includes an absorbent body and is characterized for having a first part of perforated plastic film and, on the surface which comes into contact with the user's body, a longitudinal layer which includes a second central portion of woven or non-woven material on the surface which comes into contact with the body, the first part being at least near the side edges of the absorbent body at the contact surface and having the thickness of the absorbent body.

Some observations must be made on the terms used in the former paragraph:

"absorbent product" includes any materials that are absorbent per se or that cause absorbency, the most common of which are paper, wood pulp and hydrocoloids.— "elongated" includes both flat products and products that are curved. before use.

longitudinal layer" means that the layer has its length aligned with the length of the absorbent product, but not necessarily of the same width or length.

"central portion" refers to a generically spectral shape referring to the imaginary central longitudinal axis along the length of the absorbent product.

"Non-woven" includes, needled, hydrophobic or hydrophilic non-wovens that are chemically or thermally bonded, with or without openings, of natural, artificial or synthetic fibers or mono or multilayered mixtures thereof. It is preferable to use a thermobonded web of polypropylene carded fibers.

"perforated plastic film" refers to any thin films of polymeric material, for example, polyethylene, polyurethane and. mixtures thereof and/or of other polymers, or laminates of more than one material, having any thickness or color. The openings may have any size or geometry. The film can have macro or micro protrusions embossed. in the non-perforated areas.

"first part at least near the side edges of the absorbent body" means a straight or otherwise strip, adjacent or partially superimposed or overlaid on a first part of woven/non-woven fabric. It is evident that this absorbent body has two side edges whereby there are two strips, of equal widths or otherwise, the lengths of which, when summed, preferably occupy approximately ⅕ to ⅗ of the width of the surface that comes into contact with the body, reaching up to ⅞ of this width.

"and having the thickness of the absorbent body" means that the perforated plastic film, that already covers part of the surface in contact with the body, also covers the side of the absorbent body.

The perforated plastic film that constitutes the first portion of that longitudinal layer is a substrate which begins near the side edges and on the surface of the absorbent body, and preferably continues throughout the entire thickness of the body, covering the sides as well. Optionally, the plastic film covers the back part: of the absorbent body, that is, the surface opposite that which comes into contact with the user's body and which touches the underwear.

It is important to highlight one of the advantages of the present invention over the prior art in which a central longitudinal strip of the surface of the sanitary napkin in contact with the user's body comprises a perforated plastic film, sandwiched between non-woven fabric adjacent the edges of the absorbent body. Two factors seem to favor leaking:

1. Liquid falling on the non-woven/plastic film interfaces will tend to flow towards the non-wovens (at the edges) which are less liquid repellent than the plastic film (in the center).
2. The absorbent body, when wet and squeezed between the user's legs, can force the liquid towards the longitudinal edges covered by non-woven fabric, that is to say, it is little resistant to leakage.

The product of the present invention eliminates or greatly minimizes these factors which are favorable to leakage, that is to say:

1. Liquid which reaches the non-woven/plastic film interfaces will go towards the less repellent material, or non-woven. As this is found in the center of the surface of the absorbent body, the liquid to be absorbed will tend to move away from the edges, eliminating leaks. It is obvious that the liquid that only contacts the perforated plastic film will tend to go through the orificies towards the absorbent material.
2. The absorbent body, when wet and pressed between the user's legs, may force the liquid towards perforated plastic film at the edges, which is less likely to absorb the liquid than the non-woven. This aspect is enhanced if the holes are conical, that is to say, if their diameter decreases closer to the absorbent body—and this is the form of the plastic film that is preferred in this invention.

The invention will now be described in detail based on a preferred embodiment illustrated in the accompanying drawings, in which:

FIG. 1 is a perspective view of a preferred embodiment of a sanitary napkin in accordance with this invention;

FIG. 2 is a cross sectional view of the sanitary napkin illustrated in FIG. 1.

It can be observed from FIGS. 1 and 2 that the sanitary napkin 1 of this invention is made of a substantially flat and elongated, approximately parallelepiped shaped absorbent body 2, covered. by an. external layer 3. According to this invention, this external layer 3 has a first portion 5 made of a plastic film containing orifices 6, and. a second portion 7 which comes into direct contact with the user's pubic region (not illustrated). This second. portion 7 is made up of a layer of non-woven material with orifices S.

The first portion 5 of layer 3 extends throughout the lower face of napkin 1, which faces the user's underwear, and also along the side walls 11 and. a longitudinal stretch 12 of the superior face 13 of napkin 1. The second portion 7 extends along the entire upper central longitudinal region 13, which in use contacts the skin. The first and second portions 5 and 7 overlap where they are joined together by means of an an adhesive strip along region 12.

To prevent leaking at its bottom, absorbent body 2 is protected with a liquid-impermeable barrier (not shown) at its lower face 10, between body 2 and the first portion 5 of layer 3.

According to an alternative embodiment, the first portion 5 could be a non-woven covering that is more hydrophobic than the material of second portion 7.

As the plastic film that covers the first portion 5 is opaque, the presently proposed construction is advantageous since it provides good masking, that is to say, it also partially hides any blood at the edges of the absorbent body 2, minimizing the impression of imminent leaking caused in such circumstances.

The absorbent body 2 can be made from any material that is absorbent and/or retains body exudates, such as wood pulp, bamboo fibers, cane bagasse or corn stalk or corn cob , turf moss, absorbent foams or sponges, synthetic or polymeric fibers, superabsorbent materiais (that form hydrogels when in contact with liquids) or combinations of such materials.

As is known in the art, bottom face 10 can be at least partially coated with an adhesive (not illustrated) to ensue attachment of the sanitary napkin to the user's underwear. A removable sheet (also not illustrated) protects the adhesive until the product is used. This adhesive can be in the form of one or more be longitudinal or transverse strips or bands, continuous or non-continuous lines, etc.

The present invention also does not exclude alternative embodiments in which the sanitary napkin has side flaps, used better to accomodate the napkin on the user's underwear.

It should be borne in mind that the sanitary napkin described above is merely a preferred embodiment of the present invention, the true scope of which is defined in the following claims.

We claim:

1. An absorbent product adapted to be worn in a user's undergarment including an absorbent body having a top, body-facing side and a bottom, undergarment-facing side, and a pair of opposite longitudinally extending sides, the top, body-facing side being covered by a surface layer adapted to come into contact with the user's body, the surface layer having opposite longitudinally extending first portions adjacent to and covering the opposite longitudinally extending sides of the absorbent body and a centrally located, longitudinally extending second portion, wherein the first portions are perforated plastic film and the second portion is a non-woven fabric.

2. The absorbent product according to claim 1, wherein the non-woven fabric is a thermobonded web of carded polypropylene fibers.

3. The absorbent product according to claim 2, wherein the non-woven fabric is hydrophilic.

4. The absorbent product according to claim 1, wherein the first portions of the surface layer extend to the bottom, undergarment-facing surface of the absorbent product.

5. The absorbent product according to claim 1, wherein the first portions of the surface layer cover the side edges of the absorbent body and up to approximately ⅞ of the top, body-facing surface of the absorbent body.

6. The absorbent product according to claim 1 wherein the first portions of the surface layer cover the side edges of the absorbent product between ⅕ to ⅗ of the top, body-facing surface of the absorbent body.

7. The absorbent product according to claim 1, wherein the absorbent product is a sanitary napkin.

* * * * *